(12) United States Patent
Schmidt

(10) Patent No.: US 7,989,386 B2
(45) Date of Patent: Aug. 2, 2011

(54) MULTI-LAYER CATALYST MADE FROM NIOBIUM FOR THE CATALYTIC CONVERSION OF HYDROCARBONS

(75) Inventor: Friedrich Schmidt, Rosenheim (DE)

(73) Assignee: Sud Chemie AG, Munich (DE)

( * ) Notice: Subject to any disclaimer, the term of this patent is extended or adjusted under 35 U.S.C. 154(b) by 649 days.

(21) Appl. No.: 11/995,439

(22) PCT Filed: Jul. 12, 2006

(86) PCT No.: PCT/EP2006/006844
§ 371 (c)(1),
(2), (4) Date: Jan. 11, 2008

(87) PCT Pub. No.: WO2007/006571
PCT Pub. Date: Jan. 18, 2007

(65) Prior Publication Data
US 2008/0194400 A1    Aug. 14, 2008

(30) Foreign Application Priority Data
Jul. 13, 2005 (DE) .................. 10 2005 032 723

(51) Int. Cl.
*B01J 27/25* (2006.01)
*B01J 27/188* (2006.01)
*B01J 27/185* (2006.01)
*B01J 27/045* (2006.01)
*B01J 23/32* (2006.01)
*B01J 23/00* (2006.01)
*C07C 2/00* (2006.01)
*C07C 5/00* (2006.01)
*C07C 5/13* (2006.01)
*C10G 11/18* (2006.01)

(52) U.S. Cl. ........ 502/223; 502/201; 502/210; 502/213; 502/324; 502/325; 502/351; 502/353; 585/500; 585/734

(58) Field of Classification Search .................. 502/201, 502/210, 213, 223, 324, 325, 351, 353; 585/500, 585/734
See application file for complete search history.

(56) References Cited

U.S. PATENT DOCUMENTS

| | | | |
|---|---|---|---|
| 4,582,911 A * | 4/1986 | Wachs et al. | 549/239 |
| 4,613,714 A * | 9/1986 | Stadler et al. | 585/271 |
| 5,496,788 A * | 3/1996 | Domesle et al. | 502/333 |
| 6,586,361 B1 * | 7/2003 | Heidemann et al. | 502/353 |
| 2003/0092566 A1 * | 5/2003 | Inoue et al. | 502/218 |
| 2004/0068148 A1 * | 4/2004 | Allison et al. | 585/16 |
| 2009/0011930 A1 * | 1/2009 | Hagemeyer | 502/182 |

FOREIGN PATENT DOCUMENTS

| | | |
|---|---|---|
| DE | 33 20 388 A1 * | 12/1984 |
| DE | 3320388 A1 | 12/1984 |
| WO | WO 2006/048180 A | 5/2006 |
| WO | 2009/027099 A1 * | 3/2009 |

OTHER PUBLICATIONS

"Effect of preparation method on the properties of Nb2O5 promoted platinum catalysts," Fabio B. Passos et al. Catalysis Today 43 (1998), pp. 3-9.*

"Characterization and dehydrogenation of Pt/Nb2O5 catalysts," Donato A. G. Aranda et al. Catalysis Today 28 (1996), pp. 119-125.*

Aranda, D.A., et al.; "Characterization and dehydrogenation of activity Pt/Nb2O5 catalysts"; Catalysis Today; 1996; pp. 119-125; vol. 28; XP002406919.

Tokio, I., et al.; "Acidic and catalytic properties of niobium pentaoxide"; Bulletin of the Chemical Society of Japan; Oct. 1, 1983; pp. 2927-2931; vol. 56, No. 10; XP002406920 (Tokio Iizuka, et al.).

* cited by examiner

*Primary Examiner* — Patricia L Hailey

(74) *Attorney, Agent, or Firm* — Millen, White, Zelano & Branigan, P.C.

(57) ABSTRACT

The invention relates to a multi-layer catalyst made from niobium for the catalytic conversion of hydrocarbons, comprising a) a support component made from a doped or undoped oxide or hydroxide of an element of the V sub-group of the periodic table, or mixtures thereof, b) a layer of a promoter compound, selected from oxygen, sulphur or phosphorus compounds of an element of the VI, VII and VIII sub-group or a phosphoxy compound and mixtures thereof and c) a layer comprising a compound of platinum metal. The invention further relates to a method for production of the catalyst and the use thereof.

19 Claims, No Drawings

MULTI-LAYER CATALYST MADE FROM NIOBIUM FOR THE CATALYTIC CONVERSION OF HYDROCARBONS

The present invention relates to a solid acidic catalyst comprising a plurality of chemically different layers, based on a core comprising oxides of transition group V, which is suitable for the acid-catalyzed rearrangement of hydrocarbons, for example for the hydroisomerization of paraffins. The present invention further relates to a process for preparing such a catalyst and to the use of the catalyst.

The most important refinery processes which are catalyzed by solid acids include, for example, the catalytic splitting of heavy hydrocarbon fractions, the hydrogenating splitting of heavy hydrocarbons, the removal of waxes from kerosene and diesel fractions, the alkylation of C4 fractions and the hydroisomerization of C4 to C7 fractions, and also in the field of petrochemistry, for example the alkylation or the acylation of aromatics, or the dealkylation, transalkylation and isomerization of alkylaromatics. Further important chemical processes which are catalyzed by solid acids are the esterification, the etherification, the amination or the dehydration of alcohols, the dehydration of olefins and the oligomerization of functionalized hydrocarbons. In particular, the two refinery processes for the alkylation of C4 fractions and the isomerization of higher paraffins are gaining increasing significance as important alternatives for increasing the octane number in automotive gasoline.

For some time, attempts have been made to carry out the two processes mentioned above with solid but noncorrosive acids, for example zeolites or sulfated zirconium oxide, instead of with corrosive solid acids, for example chlorinated aluminum oxide.

Typically, mordenites are used as zeolite catalysts for the noncorrosive hydroisomerization of paraffins. However, these afford the desired yields only at temperatures around 250° C., but the selectivity of the isomers achieved is not ideal. Considerably higher selectivities of the desired isomers, in contrast, are achieved only at significantly lower temperature. At this temperature, the conversion of the mordenite catalysts, compared with catalysts composed of chlorinated aluminum oxide, is too low. The disadvantage of chlorinated aluminum oxide is its extreme sensitivity even to traces of water, which causes an increased level of complexity for the purification of the starting materials.

Catalysts based on sulfated zirconium oxides exhibit (see, for example, EP 1 002 579 A1) optimal selectivities at temperatures which are below those at which zeolite-based catalysts are used, but are still significantly above the temperatures at which chlorinated aluminum oxide is employed. Catalysts based on zirconium oxide therefore require additional promotion with elements such as iron, manganese or nickel. Even these doped or promoted catalysts do not achieve the desired selectivities of catalysts based on chlorinated aluminum oxide.

Niobium compounds and materials now constitute an alternative for some applications to the customary titanium or zirconium catalysts (Niobium, Science and Technology, Proceedings Int. Symposium July 2001, Orlando, Fla., Niobium 2001 Limited, Richville, p. 269 ff.). Especially with regard to its eletronegativity and mechanisms of catalytic reactions, there are great differences between niobium and its adjacent elements in the Periodic Table, such as vanadium, zirconium and molybdenum. The catalytic action of niobium compounds is quite different from that of these elements, and therefore not foreseeable.

It is known that niobium oxides improve the catalytic activity and prolong the lifetime of the catalyst when small amounts of niobium oxides are added to known catalysts. Hydrogenated niobium pentoxide, $Nb_2O_5.nH_2O$, which is customarily also known as niobic acid, and also niobium phosphate, are strong acids and are consequently also used as an additive for solid acidic catalysts.

Since niobic acid already contains water, the water sensitivity of niobic acid compared, for example, to chlorinated aluminum oxide is extremely low.

The acid strength of niobic acid ($Ho=-5.6$) corresponds to about 70% of the acid strength of $H_2SO_4$ when niobic acid is calcined at temperatures of from about 100 to 300° C., even though the surface of niobic acid which has been calcined at 500° C. is generally neutral.

U.S. Pat. No. 4,652,544 discloses a solid catalyst consisting essentially of hydrated niobium oxide, in which the acid strength of the catalyst surface has been increased by adding phosphorous acid on its surface. This also inhibited the crystallization of the niobium oxide and delayed the loss in the catalytic activity after treatment at high temperature. This catalyst is prepared by treating hydrated niobium oxide or an anhydride thereof with a phosphorous acid. This catalyst hydrates ethylene to ethanol.

Further uses of niobium ions and niobium compounds as catalysts or catalyst components are summarized in the review articles by J. C. Vedrine, Catalysis Today, 28, 1996, 3-15 "Niobium Oxide based Materials as Catalysts for acidic and partial Oxidation Type Reactions" and by F. A. Chernyshkova, Russian Chemical Review, Volume 62, 1993, No. 8, p. 743-749 "Niobic acid,—a new Heterogeneous Catalyst for Processes in Petrochemical and Organic Synthesis". Generally, niobium compounds are used in catalysis either as additional components for already existing catalysts or for the partial oxidation of hydrocarbons.

In addition, U.S. Pat. No. 5,668,074 discloses a Lewis-acidic niobium catalyst which is highly corrosive. This catalyst is used for the isomerization of alkanes and cycloalkanes and is prepared by applying niobium or tantalum compounds to an already reduced precursor of platinum or palladium on alumina. This niobium-containing precursor is heated in a nonreducing gas and at least one fluoroalkane or chlorofluoroalkane, preferably $CClF_3$.

One disadvantage of all nonzeolitic catalysts described to date is their sensitivity to contamination by water in the starting stream.

It is therefore an object of the present invention to provide a catalyst which is based on a solid acid and is in particular less sensitive to traces of water in the reaction mixture, especially in the catalytic conversion of hydrocarbons, for example the hydroisomerization of paraffins, than the catalysts known to date, for example those based on chlorinated aluminum oxide or promoted zirconium oxide. Moreover, this catalyst should have just as excellent a low-temperature activity and just as high a selectivity as the catalysts known to date.

This object is achieved by a multilayer catalyst comprising
a) a support component comprising a doped or undoped oxide or hydroxide of an element of transition group V of the Periodic Table or mixtures thereof, arranged thereon
b) a first layer of a promoter compound selected from oxygen, sulfur, vanadium or phosphorus compounds of an element of transition group VI, VII and VIII or from main group phosphates, main group sulfates and mixtures thereof, and
c) a further layer comprising a compound of the platinum group metals.

The support component comprises either a niobium compound or a tantalum compound. The support component preferably comprises a niobium compound, most preferably niobic acid, which is substantially water-insensitive and nevertheless has a high acid strength. The inventive catalyst can be referred to as a particularly acidic catalyst which consists of specifically defined layers and enables an increased conversion, stability and selectivity especially in the isomerization of light naphtha to increase its isoparaffin content.

In very particularly preferred embodiments, the support component comprises a niobic acid doped with an alkaline earth metal or with a lanthanoid, which enhances the acid strength of the niobic acid even further.

In an advantageous embodiment, the support component further comprises a binder, for example an aluminum, silicon or zirconium compound, or mixed and unmixed oxides, sulfates or hydroxides thereof, which further increases the acid strength of the catalyst core. Examples of the inventive binder are, as well as silicon dioxide, for example, zirconium oxide, aluminum oxide, boehmite or an aluminate. Moreover, the binder enables the preparation of shaped bodies from the support components, such that it is also possible in a simple manner to realize different geometric forms for an inventive multilayer catalyst.

In a very particularly preferred embodiment of the inventive catalyst, the core of the inventive multilayer catalyst consists of niobium oxide, which further comprises a binder, for example alumina or boehmite. The proportion of binder is preferably 5-70% by weight, based on the total weight of an inventive catalyst. In general, it is preferred that the binder likewise increases the acid strength.

Although the catalyst can also be used in powder form, the addition of the inventive binder leads, especially in the case of processing to shaped bodies, to an increase in the mechanical stability and to better handling than in the case of pressing to shaped bodies without binder.

It has also been found that the activity and the selectivity of an inventive catalyst can be enhanced when a further layer is present on the support component, composed of a so-called promoter compound. The promoter component comprises phosphorus oxides and the unmixed or mixed oxides, hydroxides and sulfates, phosphates and vanadates of an element of transition group VI, VII and VIII, or from main group phosphates or sulfates and mixtures thereof. Preferred elements are molybdenum, tungsten, iron, manganese, ruthenium, rhodium and nickel. Specific nonrestrictive examples of such compounds are, for example, $(NH_4)_2SO_4$, $NH_4Fe(SO_4)_2$. Most preferably, the promoter compound is present in an amount of 5-50% by weight based on the total weight of the catalyst in the inventive catalyst.

Upon this layer of a promoter compound is applied a further layer comprising a compound of the platinum group metals, especially a compound of platinum or palladium, in an amount of from 0.01 to 3% by weight based on the total weight of the inventive catalyst, in order to enhance the activity and selectivity of the inventive catalyst even further. In addition to platinum and palladium, further preferred metals are noble metals such as gold, silver, ruthenium, rhodium, palladium, iridium and platinum. Particular preference is given to using platinum and its compounds for hydroisomerizations.

It has been found that the inventive catalyst is suitable especially for the conversion of hydrocarbons, for example hydroisomerization of paraffins, since the inventive catalyst enables the hydroisomerization to be performed at low temperatures of 140° C.-180° C., while achieving a high conversion at equilibrium and very good selectivities. An increase in the "research octane number" compared to the industrial standard of a zeolite-based catalyst by up to 5 points is achieved.

By virtue of this further layer preferably arranged on the outer surface of the catalyst, which comprises a compound of the platinum group metals, the use of the inventive catalyst for hydrogenations, dehydrogenations and hydroisomerizations is also possible in a particularly advantageous manner.

The term "layer" used in the present context encompasses both discrete, physically distinguishable layers and layers or coats merging into one another, as can form, for example, through successive impregnation of a shaped body with solutions of different compounds.

The object of the present invention is also achieved by a process for preparing a multilayer catalyst, comprising the steps of
a) dissolving a niobium-oxygen compound,
b) then adding a dilute acid until niobic acid precipitates,
d) drying the niobic acid,
e) preparing a shaped body from the dried niobic acid,
f) applying a promoter component to the shaped body,
g) applying a compound of the platinum group metals.

Preference is also given to adding a template compound in step a), which may, for example, be a quaternary ammonium compound, nonionic polyethylene oxide or a liquid crystal, such that the niobic acid can be precipitated with a controlled porosity, which provides an additional advantageous synergistic effect. A high mesoporosity achieves better accessibility of the reactants to the active sites and a shorter residence time of the intermediate, and hence suppresses further reaction (oligomerization).

Preference is given to calcining the dried niobic acid further. Moreover, after each application of a further layer, the shaped body is dried and/or calcined again. Intermediate calcination often affords a higher stability of the catalyst performance.

The process according to the invention is, for example, preferably carried out as an ion exchange process of an alkali metal niobate, for example potassium niobate $K_4Nb_6O_{17}$ with 0.5 M $HNO_3$ or sulfuric acid in aqueous solution at room temperature to give $H_4Nb_6O_{17}$ with an atomic ratio of H:Nb=2:3. Alternatively, a niobate, for example $KCa_2Nb_3O_{10}$, can be converted to $HCa_2Nb_3O_{16}$ in a ratio of H:Nb=1:3. Of course, it is equally possible to use other alkaline earth metal- and/or lanthanide-modified compounds, whose proton content (ratio of H:Nb) and acid strength (dependent on the chemical composition) are adjusted to the process to be catalyzed.

It is equally possible to carry out the process according to the invention from commercially available niobic acid which is optionally modified by swelling with the aid of organic templates as explained above and subsequent precipitation with dilute acids.

The shaping in the process according to the invention can be effected in various ways, for example by pressing or extrusion. The powder of niobic acid is extruded after addition of a binder or binder precursor, for example pseudoboehmite and optionally further peptizing agents and/or other extruding assistants. The extrudates can subsequently be dried, for example at temperatures of from 90° C. to 100° C. If appropriate, the shaped bodies can also be calcined, in which case temperatures in the range from 350° C. to 600° C. are generally used.

After the optional drying and/or calcination, preference is given to applying a layer of a catalytically active promoter component, for example compounds of catalytically active metals, preferably from group VIB, VIIB or VIIIB. These promoter components are added or applied in any manner familiar to those skilled in the art, for example by mixing, application by knife-coating, vapor deposition, or impregnation with a solution.

In preferred embodiments, the shaped body is impregnated, for example, with an appropriate solution of the promoter component. The solution may be an aqueous solution or nonaqueous solution. The impregnation solution is preferably adjusted such that the impregnation solution is taken up completely by the catalyst. This gives rise to a gradient in the concentration of the promoter component in the interior of the catalyst, such that almost only promoter component is present at the surface of the shaped body thus treated. The catalysts are subsequently dried, for example, at temperatures of from about 90° C. to 130° C. for from 5 to 20 hours, and then optionally calcined, for example, at from 350° C. to 400° C. for from 5 to 10 hours.

After the drying and/or calcination of the intermediate, preference is given to applying a further layer of a catalytically active component, for example compounds of the platinum group. Here too, the further layer of a catalytically active component is applied in any manner familiar to those skilled in the art, for example by intensive mixing, vapor deposition, knife-coating or impregnation with a solution.

Preference is given to impregnating the catalyst, for example, with an appropriate solution of a noble metal, for example with an aqueous solution of $H_2PtCl_6$ in the case of platinum. Here too, the impregnation solution is preferably adjusted such that the impregnation solution is taken up completely by the shaped catalyst body. Subsequently, the catalysts are dried, for example, at temperatures of from 90 to 130° C. for from 5 to 20 hours, and then calcined at from 350° C. to 400° C. for from 5 to 10 hours.

The inventive catalyst thus prepared is suitable for all acid-catalyzed reactions, for example the hydroisomerization of paraffins, the catalytic splitting of heavy hydrocarbon fractions, the hydrogenating splitting of heavy hydrocarbons, the removal of waxes from kerosene and diesel fractions, for the alkylation of C4 fractions, and in the field of petrochemistry, for example for the alkylation or acylation of aromatics, or the dealkylation, transalkylation or isomerization of alkylaromatics, and in the field of the remaining chemical processes of esterification, etherification, amination, or the dehydration of alcohols, the hydration of olefins, the dimerization of olefins and the oligomerization of functionalized hydrocarbons, the mild cracking of hydrocarbons, dewaxing, the hydroisomerization of Fischer-Tropsch fractions.

In a particularly preferred embodiment, the inventive catalyst thus prepared is very particularly suitable for the hydroisomerization of C4 to C7 fractions and of waxes.

The inventive catalyst is also used in the conversion of hydrocarbons. The inventive catalyst is particularly suitable for reforming cuts from mineral oil distillation, for increasing the flowability of gas oils, for isomerizing olefins or aromatic compounds, for catalytic or hydrogenating splitting, or else for oligomerization or polymerization of olefinic or acetylenic hydrocarbons. Further applications are alkylation reactions, transalkylation and isomerization or disproportionation of aromatics and alkyl-substituted aromatics, dehydrogenations or hydrogenations, hydration and dehydration, alkylation and isomerization of olefins, desulfurization, conversion of alcohols and ethers to hydrocarbons and conversion of paraffins or olefins to aromatics.

The catalyst is very particularly suitable for hydroisomerizing naphthenes. The present invention therefore especially also provides for the use of the inventive catalyst for the hydroisomerization of higher paraffins. The term "higher paraffins" is understood to mean saturated linear hydrocarbons having a carbon number of more than 4 carbon atoms.

The hydroisomerization is performed in the presence of hydrogen, preferably at temperatures below 290° C., preferably at from about 80° C. to 260° C. The pressure in the hydroisomerization is preferably within a range of from 1 to 50 bar at a liquid hourly space velocity (LHSV) of from about 0.1 to 10 liters per hour of hydrocarbon supplied or of the hydrocarbon-containing mixture per liter of catalyst.

The invention will be illustrated in detail hereinafter with reference to working examples.

EXAMPLE 1

Inventive Preparation of a Catalyst Precursor Based on Niobium Oxide 113 g (0.323 mol of Nb) of ammonium niobium oxalate $NH_4[NbO(C_2O_4)_2(H_2O)_2].(H_2O)$ (molecular weight: 350.91 g/mol) are dissolved at room temperature in 1.0 liter of water, and the solution is stirred at room temperature for 2 hours. 90 g of oxalic acid (molecular weight: 90.035 g/mol) are then dissolved in 1 liter of water at room temperature. With stirring, the ammonium niobium oxalate solution is then transferred into the oxalic acid solution. The resulting solid is filtered off from the solution and then washed with 0.25 molar nitric acid until the concentration of ammonium ions in the filtrate is less than 10 ppm. The filtercake is dried at 120° C. with ingress of air over 16 hours.

EXAMPLE 2

Inventive Preparation of Porous Shaped Bodies of a Binder-Containing Catalyst Precursor Based on Niobium Oxide For the shaping, the dried filtercake is ground with a mill to a mean particle size of 500 µm. The dried and ground filtercake is then mixed in dry form with 5 g of a commercial peptizable aluminum oxide hydrate in a kneader for 15 minutes. To this mixture are slowly added 50 ml of a 1.5% aqueous nitric acid solution and 5 ml of steatite oil, and the mixture is kneaded until a plastic, shapable material has formed and then extruded in a commercial extruder to give shaped bodies having a diameter of about 1.6 mm and a length of about 5 mm. The extrudates are dried at 120° C. for 5 hours and then calcined at 350° C. for 5 hours.

EXAMPLE 3

Promotion

The shaped catalyst body thus prepared is sprayed at room temperature with a solution of 2 g of ammonium sulfate (calculated in anhydrous form) as a promoter component in 50 ml of water with constant inversion. The catalyst is then dried at 120° C. for 15 h and then calcined at 350° C. for 5 hours.

EXAMPLE 4

Preparation of the Platinum-Containing Catalyst

For the inventive preparation of the Pt-containing catalyst, 0.35 g of a hexachloroplatinic acid solution which contains 30% by weight of Pt in 10 ml of water was added to the sulfate-containing extrudates. The mixture was mixed mechanically at room temperature and dried at 120° C. for 12 hours. The dry shaped body is calcined in air, heated to 350° C. at 100° C./h, and kept there for 3 h, and then cooled at 100° C./h.

EXAMPLE 5

100 g of a nonionic block copolymer P123 $(PEO)_{20}(PPO)_{70}(PEO)_{20}$ are dissolved in 1 liter of propanol, and then 1 mol of niobium chloride (molecular weight 270.17) is added slowly. The mixture is aged at 40° C. with stirring over 10 days. The product is removed and the template is removed at 450° C. over 7 hours.

The catalyst is processed further as described in examples 2 to 4.

EXAMPLE 6

100 g of a nonionic block copolymer P123 $(PEO)_{20}(PPO)_{70}(PEO)_{20}$ are dissolved in 1 liter of propanol, and then 0.1 mol of niobium chloride (molecular weight 270.17) is added slowly. 0.1 mol of water is added to the mixture. The mixture is then aged at 40° C. with stirring over 10 days. The product is removed and the template is removed at 450° C. over 7 hours.

The catalyst is processed further as described in examples 2 to 4.

EXAMPLE 7

100 g of a nonionic block copolymer P85 $(PEO)_{25}(PPO)_{40}(PEO)_{25}$ are dissolved in 1 liter of propanol, and 0.1 mol of niobium chloride (molecular weight 270.17) is added slowly. 0.1 mol of water is added to the mixture. The mixture is then aged at 40° C. with stirring over 10 days. The product is removed and aged further at 80° C. Thereafter, the catalyst precursor is washed in each case with 1 liter of water, dried at 120° C. for 5 hours and then calcined at 450° C. for 7 hours.

The catalyst is processed further as described in examples 2 to 4.

EXAMPLE 8

100 g of a nonionic block copolymer P85 $(PEO)_{25}(PPO)_{40}(PEO)_{25}$ are dissolved in 1 liter of propanol, and then 0.1 mol of niobium chloride (molecular weight 270.17) is added slowly. 0.1 mol of water is added to the mixture. The mixture is then aged at 40° C. with stirring over 10 days. The product is removed and aged further at 80° C. The catalyst precursor is washed three times with 1 liter of water in each case and then dried at 120° C. for 5 hours. Subsequently, the catalyst precursor is calcined at 350° C. for 7 hours.

The catalyst is processed further as described in examples 2 to 4.

EXAMPLE 9

1 mol of ammonium niobium oxalate $NH_4[NbO(C_2O_4)_2(H_2O)_2] \cdot (H_2O)$ (molecular weight: 350.91 g/mol) are dissolved at room temperature in 5 liters of water, and the solution is stirred at room temperature for 2 hours. 3 mol of oxalic acid (molecular weight: 90.035 g/mol) are then dissolved in 5 liters of water at room temperature. With stirring, the ammonium niobium oxalate solution is then transferred into the oxalic acid solution. The resulting solid is filtered off from the solution and then added to a solution of 100 g of a nonionic block copolymer P85$(PEO)_{25}(PPO)_{40}(PEO)_{25}$ dissolved in 1 liter of propanol. The mixture is then aged at 40° C. with stirring over 10 days. The product is removed and aged further at 80° C. The catalyst precursor is washed three times with 1 liter of water in each case and then dried at 120° C. for 5 hours. Subsequently, the catalyst precursor is calcined at 350° C. for 7 hours.

The catalyst is processed further as described in examples 2 to 4.

COMPARATIVE EXAMPLE 1

0.8 kilogram of hydrated niobic acid $Nb_2O_5 \cdot nH_2O$ (CBMM, brand: HY-340®) is ground in a ball mill to an average particle size of 500 μm. For the shaping of the catalyst, 0.4 kilogram of a commercial peptizable alumina hydrate as a setting agent is mixed in dry form with 0.8 kilogram of the ground niobic acid in a kneader for 15 minutes. To this mixture are slowly added 0.1 kilogram of a 1.5% by weight aqueous nitric acid solution and 10 ml of steatite oil, and the mixture is kneaded until plastification. The material is then pressed through an extrusion plate which contains bores such that the extrudates, after drying, have a diameter of 1.5 mm. The extrudates are dried at 120° C. for 5 hours and then calcined at 350° C. for 5 hours, with a ramp of 100° C./h to 350° C., kept at 350° C. (550° C., 450° C.) for 4 h, and then cooled at 100° C./h.

A solution of 0.35 g of the hexachloroplatinic acid solution which contains 30% by weight of Pt in 10 ml of water was added to the calcined extrudates. The mixture was mixed mechanically at room temperature and dried at 120° C. for 12 hours. The dried shaped body is calcined in air, at 100° C./h up to 350° C. (550° C., 450° C.), kept there for 3 h and cooled at 100° C./h.

COMPARATIVE EXAMPLE 2

800 g of zirconium hydroxide (MEL XZO632/03) are mixed in a kneader (Werner & Pfleiderer, Z-Kneter) with 500 g of ammonium zirconium carbonate solution (20%, MEL) and 300 g of ammonium sulfate, and kneaded for 10 min. 40 g of Methocell (cellulose ether, DOW), 50 g of steatite oil and 30 g of demineralized water are then added successively to the liquid mixture with kneading. The resulting mixture is blown with cold air for 45 min until the material achieves a consistency such that it can be extruded. The resulting mixture is extruded (extruder from Fujio Paudal Co. Ltd.; model EXKFs-1, speed setting 0.4). The diameter of the extrudates is 1.6 mm. The extrudates are dried in a drying cabinet at 80° C. for 15 hours and then calcined with the following temperature program: (1) heating from room temperature to 550° C. at a heating rate of 200° C./h, (2) holding at 550° C. for 3 hours, (3) cooling from 550° C. to RT at a rate of 200° C./h.

The extrudates are impregnated with a solution of hexachloroplatinic acid at room temperature so as to obtain a Pt content on the finished calcined catalyst of 0.5% by weight.

Subsequently, the Pt-impregnated extrudates are dried at 80° C. in a drying cabinet for 15 hours and then calcined with the following temperature program: (1) heating from room temperature to 550° C. at a heating rate of 200° C./h, (2) holding at 550° C. for 3 hours, (3) cooling from 550° C. to room temperature at a rate of 200° C./h.

WORKING EXAMPLE 1

The Pt-containing catalysts obtained according to examples 4 to 9 and comparative examples 10 and 11 were tested in a microreactor with pure n-pentane. The test conditions were as follows:

| | |
|---|---|
| Reactor diameter | 8 mm |
| Catalyst weight | 2.0 g |
| Catalyst particle size (screen fraction of the granulated material) | from 0.5 to 1 mm |
| Pressure | 20 bar |
| Temperature | 120 to 250° C. |
| Hydrogen | 20.71 ml (STP)/min |
| n-Pentane | 0.107 ml (STP)/min |
| LHSV | 2 h-1 |
| H2:n-pentane (molar) | 1:1 |

The analysis is effected by means of an on-line GC, in which a measurement point is detected every 15 minutes.

The reactor was started up as follows: first, air was introduced at a rate of 33.33 ml/min, then the reactor was heated from room temperature to 350° C. This temperature was maintained for 1 hour and then the temperature was lowered from 350° C. to 250° C. The air stream was then interrupted and replaced by a nitrogen stream (33.33 ml/min) for 30 min. The nitrogen stream was subsequently replaced by a hydrogen stream (33.33 ml/min). The pressure was then increased to 30 bar of $H_2$, and pure n-pentane was introduced. The product stream was analyzed by gas chromatography every 30 minutes. After 8 hours, the temperature was lowered to 200° C. and the catalyst was tested for 8 hours, followed by a further decrease in the temperature to 150° C. and a corresponding test for 8 hours, and the temperature was finally raised to 250° C. and the catalyst was tested for 8 hours in order to clarify any catalyst deactivation occurring in the course of time.

DEFINITIONS i-C5 activity:=% by wt. of i-$C5^P$/(% by wt. of i-$C5^P$+ n-$C5^P$)*100;
% splitting products:=% by wt. of C1-C4 hydrocarbons
n.d.:=not detectable The results for the temperature of 200° C. are listed below:

| Catalyst | i-C5 activity | % splitting products | run time (h) |
|---|---|---|---|
| Example 4 | 74.6 | n.d. | 120 |
| Example 5 | 74.8 | 0.2 | 80 |
| Example 6 | 75.0 | 0.3 | 80 |
| Example 7 | 74.6 | 0.1 | 80 |
| Example 8 | 75.5 | 0.05 | 80 |
| Example 9 | 75.7 | n.d. | 120 |
| Example 10 | 25 | 3.0 | 80 |
| Example 11 | 72.4 | 2.5 | 80 |

The thermodynamic equilibrium is at an i-C5 activity of approx. 75.7%.

The invention claimed is:

1. A multilayer catalyst for catalytic conversion of hydrocarbons, comprising
    a) a support component comprising a doped or undoped oxide or hydroxide of niobium or tantalum or mixtures thereof, arranged thereon
    b) a first layer of a promoter compound selected from oxygen, sulfur, vanadium or phosphorus compounds of an element of transition group VI, VII and VIII or from $(NH_4)_2SO_4$, $NH_4Fe(SO_4)_2$ and mixtures thereof
    c) a further layer comprising a compound of the platinum group metals,
    wherein the support component further comprises a binder comprising an aluminum, silicon or zirconium mixed or unmixed oxide, sulfate, or hydroxide or mixture thereof, wherein the amount of binder is 5-70% by weight based on the total weight of catalyst.

2. The multilayer catalyst as claimed in claim 1, wherein the amount of promoter compound is 5-50% by weight based on the total weight of catalyst.

3. The multilayer catalyst as claimed in claim 1, wherein the amount of platinum metal compound is from 0.01 to 3% by weight based on the total weight of catalyst.

4. The multilayer catalyst as claimed in claim 3, wherein the platinum metal compound is selected from the metals, the alloys thereof with one another, and oxides of the platinum group metals and mixtures thereof.

5. The multilayer catalyst as claimed in claim 4, wherein the platinum metal compound is platinum.

6. The multilayer catalyst as claimed in claim 1, wherein the support component comprises niobic acid.

7. The multilayer catalyst as claimed in claim 6, wherein the support component is a niobic acid doped with an alkaline earth metal or lanthanoid.

8. A process for preparing a multilayer catalyst as claimed in claim 1, comprising
    a) dissolving a niobium-oxygen compound,
    b) then adding a dilute acid until niobic acid precipitates,
    c) drying the niobic acid,
    d) preparing a shaped body from the dried niobic acid,
    e) applying a promoter component to the shaped body,
    f) applying a compound of the platinum group metals,
    wherein a binder is added before d), the binder being zirconium-, titanium-, or aluminum-containing mixed or unmixed oxide, sulfate or hydroxide or mixture thereof such that the amount of binder is 5-70% by weight based on the total weight of catalyst.

9. The process as claimed in claim 8, wherein a template compound is also added in a).

10. The process as claimed in claim 9, wherein the template compound is a quaternary ammonium compound.

11. The process as claimed in claim 8, wherein the niobic acid dried in c) is calcined further.

12. The process as claimed in claim 8, wherein the multilayer catalyst is dried and/or calcined after e) and/or f).

13. The process as claimed in claim 8, wherein the promoter component is a phosphorus oxide, or a mixed or unmixed oxide, hydroxide, phosphate or sulfate of an element of transition group VI, VII and VIII, or a mixture thereof.

14. The process as claimed in claim 8, wherein the platinum metal compound is a metal, an alloy thereof with another metal, an oxide of the platinum group metals or mixtures thereof.

15. A method for converting hydrocarbons comprising employing a catalyst of claim 1.

16. A method for isomerizing paraffins comprising employing a catalyst of claim 1.

17. A method for dimerizing or oligomerizing olefins comprising employing a catalyst of claim 1.

18. A method for splitting higher olefins comprising employing a catalyst of claim 1.

19. A method for reacting olefins with paraffins to form isooctane comprising employing a catalyst of claim 1.

* * * * *